United States Patent
Wen et al.

(10) Patent No.: US 10,213,521 B2
(45) Date of Patent: Feb. 26, 2019

(54) USEFUL POLYSACCHARIDE AFTER RADIATION STERILIZATION

(71) Applicant: Medtronic Xomed, Inc., Jacksonville, FL (US)

(72) Inventors: Jie Wen, St. Johns, FL (US); Denise E. Guenther, Jacksonville, FL (US); Dana A. Oliver, Jacksonville, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 12 days.

(21) Appl. No.: 14/736,750

(22) Filed: Jun. 11, 2015

(65) Prior Publication Data

US 2016/0361460 A1 Dec. 15, 2016

(51) Int. Cl.
*A61L 26/00* (2006.01)
*C08B 37/08* (2006.01)
*B65B 55/08* (2006.01)
*B65B 63/08* (2006.01)
*C08J 3/28* (2006.01)

(52) U.S. Cl.
CPC ......... *A61L 26/008* (2013.01); *A61L 26/0023* (2013.01); *A61L 26/0076* (2013.01); *B65B 55/08* (2013.01); *B65B 63/08* (2013.01); *C08B 37/003* (2013.01); *C08J 3/28* (2013.01)

(58) Field of Classification Search
CPC ........ C08B 37/003; C08J 3/28; A61L 26/008; A61L 26/0023; A61L 26/0076; B65B 55/08; B65B 63/08
USPC .......................................................... 514/55
See application file for complete search history.

(56) References Cited

U.S. PATENT DOCUMENTS

| | | | |
|---|---|---|---|
| 5,958,436 A * | 9/1999 | Hahn | A61K 8/0208 424/401 |
| 6,946,098 B2 * | 9/2005 | Miekka | A23L 3/263 422/22 |
| 7,098,194 B2 | 8/2006 | Chenite et al. | |
| 8,530,632 B2 | 9/2013 | Tijsma et al. | |
| 8,653,319 B2 | 2/2014 | Amery et al. | |
| 8,802,652 B2 * | 8/2014 | Myntti | A61K 9/0024 514/55 |

FOREIGN PATENT DOCUMENTS

| | | |
|---|---|---|
| WO | WO 2009/132225 A2 | 10/2009 |
| WO | WO 2009/132228 A1 | 10/2009 |

OTHER PUBLICATIONS

Willard et al, Instrumental Methods of Analysis, 5th Ed., 1974, pp. 226-228.*
Strlic, M. et al., European Polymer Journal, 2000, 36, 2351-2358.*
Liu, G. et al., "Synthesis and Characterization of Chitosan/Dextran-Based Hydrogels for Surgical Use", Macromal. Symp., 279, pp. 151-157 (2009).
"Controlling of Degradation Effects in Radiation Processing of Polymers", IAEA International Atomic Energy Agency, 232 pages (May 2009).
International Search Report and Written Opinion for PCT/US2016/036367 dated Sep. 9, 2016.

* cited by examiner

*Primary Examiner* — Ganapathy Krishnan
(74) *Attorney, Agent, or Firm* — Patterson Thuente Pedersen, P.A.

(57) ABSTRACT

A purified and sterilized polysaccharide that exhibits enhanced and extended shelf life over conventionally prepared polysaccharides for biomedical applications. The polysaccharide, upon crosslinking, forms a hydrogel that functions as a protective coating or on tissue and structures in the ears, nose, throat, limbs and spinal column.

15 Claims, 2 Drawing Sheets

USEFUL POLYSACCHARIDE AFTER RADIATION STERILIZATION

FIELD OF THE INVENTION

This invention relates to polysaccharides with enhanced shelf life for use in biomedical applications, including protective coatings.

BACKGROUND

Hydrogels are often utilized after surgical procedures as a biomedical protective coating to control bleeding and to reduce post-surgical adhesion. In certain applications, the hydrogels are formed by crosslinking a solubilized polysaccharide and combining it with a second solution. The hydrogel may be formed externally, or in situ after application onto a treatment site. The polysaccharide must be sterilized before its application. Sterilization at the point of use is not practical due to the activity level and complex nature of a surgical facility. In that regard, sterilization of both components of the two component system are addressed at the packaging phase of the components. However, the shelf life stability of the polysaccharide is currently limited. Current polysaccharides utilized in hydrogel applications have a limited shelf life. For example, certain polysaccharides may be limited to a shelf life of six months or less, and some circumstances, four months or less.

SUMMARY OF THE INVENTION

As set forth in this disclosure, sterilization of the polysaccharide for biomedical applications is one of the primary causes for poor shelf-life stability. The sterilization process often employs ionizing radiation, such as E-beam radiation. The radiation process breaks the chains of DNA in living organisms, such as bacteria, resulting in microbial death and rendering sterile product. Unfortunately, the radiation has a tendency to adversely affect the polysaccharide. As a result, large amounts of radicals may form in the material which can eventually lead to chain scission or chain crosslinking. Most radicals have a very short half-life and therefore can decay quickly. This decay will result in a reduction of the molecular weight of the polysaccharide. The lower molecular weight means that the viscosity will be negatively impacted and thus make it more difficult to form a hydrogel. Additionally, some long-lived radicals may be trapped in the polysaccharide for an extended period of time and subsequently alter the material characteristics. The long-lived radicals can further degrade the polysaccharide over time and may cause crosslinking resulting in insoluble material.

This disclosure is directed to a purified and sterilized polysaccharide that exhibits enhanced and extended shelf life over conventionally prepared polysaccharides for biomedical applications. The polysaccharide, upon hydrating and crosslinking, forms a hydrogel that is functional for many biomedical applications, including, but not limited to, surgical implants and as a protective coating or on tissue and structures in the ears, nose, throat, limbs and spinal column. Consistent gelling of the polysaccharide is desirable in most embodiments. Any inconsistencies in the formation of a hydrogel can negatively impact the desired biomedical results needed to address the health of the individual upon which the hydrogel is applied.

The polysaccharide is prepared by removing at least some impurities from the composition that are generally present due to its formation process. Control of the moisture content and limited exposure to oxygen also assist in enabling a longer shelf life. The material is dried to a moisture content of 7% by weight or less. The polysaccharide is then packaged in an oxygen reduced environment. The packaged polysaccharide is subjected to a sterilization process employing ionizing radiation. This method results in a polysaccharide that exhibits an improved shelf life over conventional polysaccharides. In certain embodiments, the shelf life of the polysaccharide may be extended to greater than nine months, greater than one year, and even greater than two years.

In one aspect, a two-part composition is created utilizing the purified and sterilized polysaccharide of this disclosure. Accordingly, the first part comprises a purified and sterilized polysaccharide and the second part comprises a sterilized co-reactant. Both parts may be provided in sealed packaging. The two parts, when hydrated, can mix and react with one another to form a thin, conformal protective layer on a body tissue or structure.

The disclosed composition desirably may be packaged in a multicomponent spray dispenser with the polysaccharide-containing part in dry (e.g., powdered or lyophilized) form, hydrated at or close in time to the point of use, and quickly mixed with the further sterilized co-reactant part and applied or used in a desired target area on a body tissue or body structure. The mixed parts are a fluid (viz., ungelled) when the mixture travels through the spray applicator, and may react and eventually form a gel (e.g., by the time it lands on the target area or a few minutes thereafter) or may remain a fluid when on the target area.

The disclosed composition, protective layer and method are especially useful for treating mucosal tissues in the ears, nose or throat and openings, recesses, passageways or joints in the limbs or spinal column. In some embodiments, the applied composition will not drip or run from a target area to which it has been spray-applied. By employing a polysaccharide and mixing it with a sterilized co-reactant to form a low viscosity or semi-viscous fluid rather than a much more viscous, non-sprayable gel, a sprayable composition may be dispensed through a spray device in fluid form, applied to a target area to form a fluid or only recently gelled protective layer, and kept substantially or completely in place on the target area.

DETAILED DESCRIPTION

Figure 1:
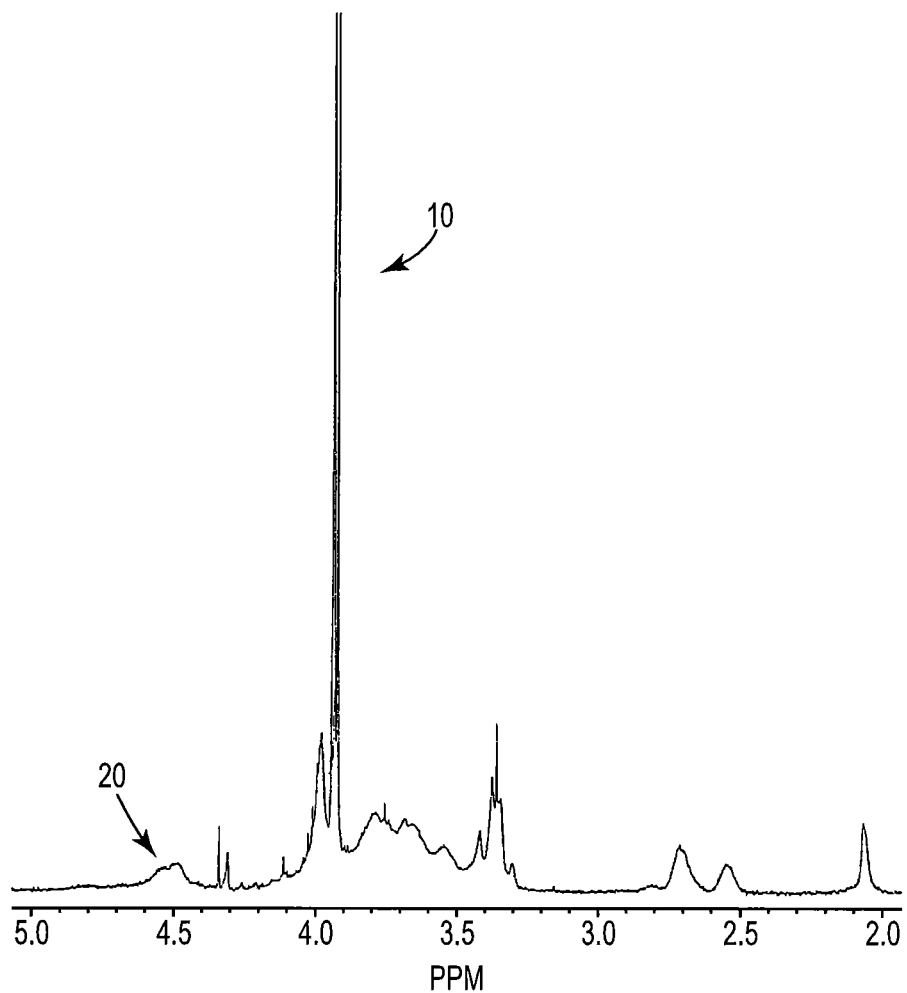
FIG. 1 is an illustration of a $^1$H NMR spectrum of carboxymethyl chitosan containing levels of impurities.

The following detailed description describes certain embodiments and is not to be taken in a limiting sense. All weights, amounts and ratios herein are by weight, unless otherwise specifically noted. The terms shown below have the following meanings:

The term "adhesion" refers to the sticking together of a body structure or prosthetic material to tissue, to the sticking together of tissue to tissue with which it is in intimate contact for extended periods, or to the formation of tissue that connects body structures, prosthetic materials or tissues to one another across a normally open space.

The term "antimicrobial" refers to an ability to cause greater than a 90% numeric reduction (viz., at least a 1-log order reduction) in a population of one or more of *Staphy-*

*lococcus aureus, Pseudomonas aeruginosa, Streptococcus pneumonia, Haemophilus influenzae, Moraxella catarrhalis, Staphylococcus epidermidis, Echerichia coli, Citrobacter freudii, Enterobacter aerogenes, Klebsiella pneumonia, Proteus mirabilis, Serratia marcescens, Staphylococcus saprophyticus, Micrococcus luteus, Streptococcus mutans, Corynebacterium diphtheria,* or *Corynebacterium tuberculostearicum*

The term "biocompatible" when used in reference to a substance means that the substance presents no significant deleterious or untoward effects upon the body.

The term "body temperature" when used in reference to a mammal means the normal rectal temperature (for example, for a human about 37° C.; for a cat, cow, dog or horse about 38° C.; and for a sheep about 39° C.).

The term "comminuted" when used in reference to a particulate material means that the particles have been fractured and reduced in size by cutting, grinding, pulverizing, triturating or other particle fracturing process employing externally-applied force.

The term "conformal" when used in reference to a composition applied to tissue or other body structure means that the composition can form a substantially continuous layer over an area to which the composition has been applied.

The term "fluid" when used in reference to a substance means that the substance is a liquid having a loss modulus (G") greater than its storage modulus (G') and a loss tangent (tan δ) greater than 1.

The term "gel" when used in reference to a substance means that the substance is deformable (viz., is not a solid), G" is less than G' and tan δ is less than 1.

The term "gelation" when used with respect to formation of a gel layer means the time at which G" equals G' and tan δ equals 1.

The term "hemostat" means a device or material which stops blood flow or promotes clotting.

The term "hydrogel" when used in reference to a gel means that the gel is hydrophilic and contains water.

The term "hydrated" when used in reference to a device or substance means that the device or substance contains uniformly distributed chemically-bound water. A "fully hydrated" device or substance is incapable of taking up additional water of hydration. A "partially hydrated" device or substance is capable of taking up additional water of hydration.

The term "mucoadhesive" when used in reference to a device or substance means that the device or substance will adhere to the mucus covering epithelia.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharynx.

The term "oxygen reduced" means an environment with less than 2% oxygen by volume.

The term "crosslinked" when used in reference to a polysaccharide means that two or more molecules of the polysaccharide have been joined to form an oligomeric or polymeric moiety which is a fluid when hydrated and which is capable of further crosslinking in situ.

The term "polysaccharide" includes derivatives of polysaccharides and modified polysaccharides, as well as derivatives of individual polysaccharide species and modified individual polysaccharide species. For example, the term "carboxymethylcellulose" includes carboxymethylcellulose derivatives and modified carboxymethylcelluloses, the term "chitosan" includes chitosan derivatives and modified chitosans, and the term "starch" includes starch derivatives and modified starches.

The term "protective" when used in reference to a layer of a composition atop tissue or other body structure means that the layer may assist in returning an injured, inflamed or surgically repaired tissue surface to a normal state, e.g., through one or more healing mechanisms such as modulation of an inflammatory response, phagocytosis, mucosal remodeling, reciliation or other full or partial restoration of normal function.

The term "residence time" when used in reference to a protective gel layer atop tissue or other body structure means the time period during which the gel layer or portion thereof remains in place in vivo under gross observation.

The term "shelf life" refers to the time after sterilization that the polysaccharide remains viable and capable of forming a hydrogel upon hydration and upon the mixture and reaction with a sterilizing co-reactant. In certain circumstances, the shelf life of the polysaccharides of this disclosure exhibit no substantial change in time to form a gel after mixing with a sterilized co-reactant.

The term "sterilized co-reactant" means a compound employed in the second part of the disclosed two-part composition, and which enables crosslinking the disclosed polysaccharide.

The term "substantially vertical" when used in reference to a skin surface refers to a surface whose orientation is 90±10° with respect to the horizontal. This phrase is not meant to imply that the disclosed compositions are applied only to substantially vertical surfaces or only to skin surfaces. Applicants have however determined that a substantially vertical skin surface may be used to evaluate certain rheological characteristics of the disclosed compositions during and promptly after spray application, without the need for complex instruments or other measuring devices or techniques.

The term "thin" when used in reference to a protective layer atop tissue or other body structure means having an average thickness less than about two millimeters.

This disclosure is directed at enhancing the shelf life of certain biomaterials, and in particular polysaccharides, post sterilization. Conventional polysaccharides generally exhibit a limited shelf life after sterilization of typically less than six months and some even less than four months. Common characteristics of conventionally prepared polysaccharides that indicate a limited shelf life include a loss of viscosity after sterilization and the development of insoluble materials. A polysaccharide produced in accordance with the method of this disclosure exhibits reduced degradation and viscosity loss and as a result is capable of achieving an increased shelf life e.g. greater than nine months. In certain embodiments, the shelf life of the polysaccharide may exceed one year, eighteen months, or even two years.

The method of this disclosure addresses the viscosity loss over time and the development of insoluble materials during storage. The method comprises removing at least some impurities from the polysaccharide. The material is then dried to a moisture content of 7% by weight or less and packaged in an oxygen reduced environment. The polysaccharide is then sterilized with ionizing radiation.

A wide variety of polysaccharides or their derivatives may be employed in the disclosed method, composition and protective layer. Non-limiting examples of polysaccharides include alginates, carrageenans, celluloses (for example, hydroxyethylcellulose, hydroxypropylcellulose, methylcellulose and hydroxypropylmethylcellulose), chitins, chitosans, carboxymethyl chitosan, chitosan succinamide, chondroitin sulfates, dextrans, galactomannans, glycogens, hyaluronic acids, starches, heparin and other biocompatible polysaccharide derivatives and mixtures thereof.

Certain embodiments utilize chitosan (including salts and other chitosan derivatives) as the polysaccharides. Exemplary chitosans and their salts (including citrate, nitrate, lactate, phosphate, chloride and glutamate salts) may be obtained from a variety of commercial sources including KitoZyme S.A., Fluka Chemie AG, the NovaMatrix unit of FMC BioPolymer AS, Heppe Medical and Sigma-Aldrich Co. Chitosan may also be synthesized by elimination of N-acetyl groups through deacetylation of chitin (poly-N-acetyl-D-glucosamine) by hydrolysis. The resulting oligomer or polymer has a plurality of repeating units (e.g., about 2 to about 10,000 repeating units, about 60 to about 600 repeating units, or such other amount as may be desired for the chosen end use). Some or all of the repeating units will contain deacetylated amino groups (e.g., about 30 to about 100% or about 60 to about 100% of the total repeating units), with the remaining repeating units (if any) containing acetylated amino groups.

Chitosan is a cationic polymer composed of glucosamine monomers, and may have a variety of number average molecular weights, e.g., about 400 to about 2000 kDa, about 10 to about 500 kDa, or about 10 to about 100 kDa. The chitosan may for example be an ultralow molecular weight material having a number average molecular weight less than about 50 kDa, a low molecular weight material having a number average molecular weight of about 50 to about 200 kDa, a medium molecular weight material having a number average molecular weight of about 200 to about 500 kDa or a high molecular weight material having a number average molecular weight greater than about 500 kDa.

Chitosan derivatives may also be employed. Non-limiting examples of derivatives include those in which one or more chitosan hydroxyl or amino groups have been modified for the purpose of altering the solubility or mucoadhesion characteristics of the derivative. Exemplary derivatives include thiolated chitosans, and non-thiolated chitosan derivatives such as carboxymethyl, acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolating reactant.

Many of the polysaccharides capable of forming a hydrogel contain various levels of impurities largely due to the manufacturing processes used to make the compositions. The impurities may include an organohalide compound, a glycolic acid or a salt or ester thereof, or an inorganic salt. The impurities can have an impact on the polysaccharide after sterilization. For example, the presence of certain impurities may act as plasticizers and thereby increase the mobility of the polysaccharide. This may lead to additional crosslinking of the polysaccharide during storage. The method of this disclosure utilizes at least one of filtration, membrane dialysis or precipitation to remove at least a portion of the impurities from the polysaccharide. Those of ordinary skill in the art with knowledge of this disclosure are capable of selecting an appropriate purification method, or combination of methods, based upon a selected polysaccharide and the acceptable level of impurities to prevent additional crosslinking of the polysaccharide in storage.

In certain embodiments, the level of impurities in the polysaccharide may be detected using $^1$H NMR spectroscopy. The removal of at least a portion of impurities by filtration, membrane dialysis, precipitation or combinations thereof may result in an integration ratio, according to $^1$H NMR spectroscopy, of 1 or less. For purposes of this disclosure, the integration ratio is determined by the value of a peak at about δ 3.92 ppm through δ 3.94 ppm to a value of a reference peak of about δ 4.5 ppm. The region between δ 3.92 ppm to δ 3.94 ppm is an indication of contamination by compounds such as chloroacetic acid and more often glycolic acid. An absence of sharp peaks at δ 3.92 ppm through δ 3.94 is an indicator of substantial or complete removal of the two noted impurities. The peak at δ 4.5 ppm is assigned to the proton at the 1-C position, which is used as a reference for the integration ratio. In one embodiment, carboxymethyl chitosan, prior to any purification, may exhibit an integration ratio of about 5.03. A purified version of carboxymethyl chitosan may have an integration ratio of less than 0.7.

FIG. 1 is an illustration of a $^1$H NMR spectrum of carboxymethyl chitosan prior to purification. The peak 10 in the δ 3.92 ppm through δ 3.94 range indicate the presence of chloroacetic acid or glycolic acid. The integration ratio, as calculated using the peak 20 in the δ 3.92 ppm through δ 3.94 range in relation to the peak at δ 4.5 ppm, is about 4.65.

Figure 2:
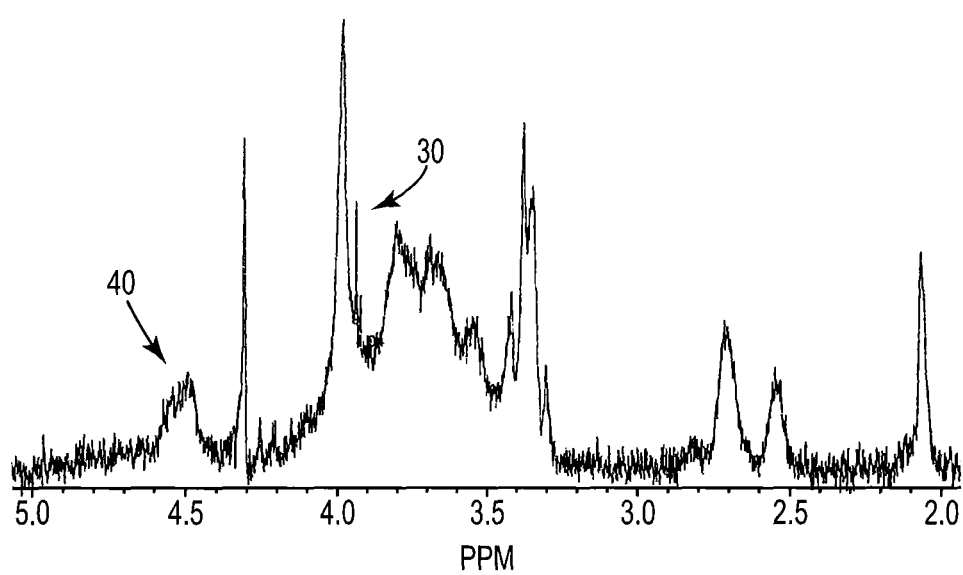
FIG. 2 is an illustration of a $^1$H NMR spectrum of a purified carboxymethyl chitosan.

FIG. 2 is an illustration of a $^1$H NMR spectrum of carboxymethyl chitosan purified using membrane dialysis. The peak 30 in the δ 3.92 ppm through δ 3.94 range indicate the presence at least some chloroacetic acid or glycolic acid. The integration ratio as calculated using the peak 30 in the δ 3.92 ppm through δ 3.94 range in relation to the peak 40 at δ 4.5 ppm is about 0.59.

Drying is employed in the method of this disclosure to remove moisture from the polysaccharide. The presence of moisture during subsequent sterilization with ionizing radiation may degrade the polysaccharide due to one or more reactions such as fragmentation, hydrolysis, or rearrangement. The drying of the polysaccharide may include lyophilization, convection drying, vacuum drying or a combination thereof. The actual form of drying may be selected based upon the purification process utilized in a prior step. For example, purification of a polysaccharide with membrane dialysis will render an at least partially purified form of the material in solution. One of ordinary skill in the art will recognize that lyophilization is a drying method well suited to recover the polysaccharide in solid form from solution for subsequent use. The moisture content of the polysaccharide after drying is less than 7% by weight. In other embodiments, the moisture content of the polysaccharide is less than 5% by weight, less than 3% by weight or even less than 1% by weight.

The polysaccharide in dried particulate form may be further modified to enable timely hydration at the point of application. In various embodiments, the polysaccharide may be comminuted. For example, the particles may be fractured and reduced in size by cutting, grinding, pulverizing, triturating or other particle fracturing process employing externally-applied forces. The polysaccharide desirably is provided in dry particulate form, for example, as free-flowing granules whose average particle diameter is less than about 1 mm, less than about 100 μm, about 1 to about 80 μm, or less than 1 μm.

The oxidative degradation of polysaccharides over time is another factor that may reduce the shelf life of the polysaccharide. Radiation induced radicals that are trapped in the semi-crystalline domains can undergo an oxidative chain reaction through a peroxide radical mechanism leading to degradation. The chain reaction can prolong for days or even months.

Such degradation due to oxygen during post sterilization and storage may be addressed by packaging the polysaccharide in an oxygen reduced environment. The polysaccharide in powder form is placed into a container, such as a syringe, vial or other container capable of enabling subsequent hydration. The container may additionally be sealed in a polymeric enclosure to further limit the penetration and exposure to oxygen. Those of ordinary skill in the with knowledge of this disclosure will recognize that other conventional methods of packaging utilizing a purge of an inert gas may be suitable to create an oxygen reduced environment.

The purified polysaccharide having a reduced moisture content and packaged in an oxygen reduced environment is sterilized using ionizing radiation. A variety of ionizing radiation sterilization sources may be employed, including gamma radiation, ultraviolet light, X-rays and E-Beam radiation. E-Beam radiation may be especially desirable due in part to the rapid rate at which it can be performed, with typical sterilization cycles usually being completed in a manner of minutes (e.g., two five minute cycles). X-rays may be preferred for applications where greater penetrating power than that provided by E-Beam radiation is required. Ultraviolet radiation and gamma radiation may also be employed, but may be contraindicated in some cases due in part to the higher degree of polymer degradation that ultraviolet or gamma radiation may cause and in the case of gamma radiation due to the much longer sterilization cycles (e.g., several hours or more) which may be required. Additionally, cold ionizing radiation sterilization (e.g., cold E-Beam sterilization) may be employed such as that disclosed in U.S. Pat. No. 8,653,319, herein incorporated by reference in its entirety.

The polysaccharide prepared in accordance with the method of this disclosure exhibits an improved shelf life. The method of this disclosure is based on the discovery that certain impurities in the polysaccharide, moisture, and oxygen can cause continued crosslinking after sterilization and thereby adversely affect the viability of the polysaccharide over time. For purposes of this disclosure, the shelf life refers to the time after sterilization that the polysaccharide remains viable and capable of forming a hydrogel upon hydration and upon the mixture and reaction with a sterilized co-reactant. In certain embodiments, the polysaccharide exhibits a shelf life of greater than nine months. In other embodiments, the polysaccharide exhibits a shelf life greater than one year, greater than eighteen months, or even greater than 2 years. The improved shelf life is a significant gain over conventional polysaccharides used in biomedical hydrogel applications.

A quantitative measure for improved shelf life of a polysaccharide may include a measure of the reduction, or change, of the viscosity of a hydrated polysaccharide over time. The Viscosity Test Method set forth in the Examples section of this disclosure is one test capable of demonstrating that the method of this disclosure results in a polysaccharide having an improved shelf life. According to the Test Method, the polysaccharide of this disclosure exhibits a reduction in viscosity of less than 50% after being retained for nine months at room temperature. In some embodiments, the polysaccharide of this disclosure exhibits a viscosity reduction of less 25%, less than 10%, or less than 5% under the Viscosity Test Method.

Another suitable measure for the improvement of shelf life of the polysaccharide is the utilization of thermal gravimetric analysis to determine the change in solids content of the polysaccharide over time. This procure can detect if crosslinking of the polysaccharide has occurred over the storage period. The procedure for the Percent Solids measurement using thermal gravimetric analysis is set forth in the Examples section of this disclosure. According to the Test Method, a polysaccharide resulting from the method of this disclosure exhibits less than a 50% change in solids content of the polysaccharide after being retained for nine months at room temperature. In some embodiments, the polysaccharide exhibits less than a 25% change in solids content, less than a 10% change in solids content, or even less than a 5% change in solids content.

The polysaccharide of this disclosure is suitable for forming a two-part composition, the first part comprising a sterilized polysaccharide produced by the method of this disclosure in sealed packaging and the second part comprising a sterilized co-reactant in sealed packaging. The two parts when hydrated may in some embodiments be sprayable fluids deliverable through a spray applicator and which will react with one another to provide a thin, conformal, non-dripping protective layer fluid on a body tissue or structure. The two parts may be hydrated, mixed and reacted utilizing conventional instruments such as those disclosed in U.S. Pat. No. 8,530,632, herein incorporated by reference in its entirety.

The second part of the two-part composition, the sterilized co-reactant, promotes crosslinking in the polysaccharide. Exemplary sterilized agents include genipin, an oxidized polysaccharide such as oxidized starch or dextran, or glutaraldehyde, or other reagents containing multiple aldehyde groups. The amount of sterilized agent may vary widely depending upon the chosen polysaccharide and sterilized co-reactant.

When an oxidized polysaccharide is used as the sterilized co-reactant, the polysaccharide may be oxidized to an extent sufficient to provide aldehyde groups capable of crosslinking the purified and sterilized polysaccharide. The polysaccharide may if desired be oxidized to a different (e.g., a greater) extent and an adjustment (e.g., an increase) made in the polysaccharide amount. In certain applications, the crosslinking of the polysaccharide is substantially complete within a few minutes or seconds (e.g., less than 5 minutes, less than 2 minutes, less than 1 minute or less than 30 seconds) after mixing with the sterilized co-reactant.

A wide variety of oxidized polysaccharides may be employed, including oxidized alginates, carrageenans, celluloses (e.g., hydroxyethylcellulose, hydroxypropylcellulose, methylcellulose and hydroxypropylmethylcellulose), chitins, chondroitin sulfates, dextrans, galactomannans, glycogens, hyaluronic acids, starches and other biocompatible polysaccharides capable of being oxidized. Oxidized polysaccharides such as oxidized cellulose (e.g., those mentioned above), chitin, chondroitin sulfate, dextran, glycogen, hyaluronic acid and starch are especially preferred. Representative oxidizing agents or techniques for preparing oxidized polysaccharide include the use of a) sodium periodate, b) hypochlorite ion in the presence of di-tert-alkylnitroxyl catalysts, c) metal-catalyzed oxidation, using for example ruthenium, d) anhydrous oxidation using for example nitrogen dioxide in for example a halocarbon, e) enzymatic or chemo-enzymatic oxidation of starch, guar and other polysaccharides, f) 2,2,6,6-tetramethylpiperidine-1-oxyl (TEMPO) catalyzed oxidation with mild oxidants such as dimethylsulfoxide (DMSO) or diacetoxyiodobenzene, and other oxidation agents and techniques that will be known to persons having ordinary skill in the art.

In some embodiments, the sterilized co-reactant may be dried and purified in a manner similar to those used to dry and purify the polysaccharide. Similar to the polysaccharide of this disclosure, the drying, purifying, of the sterilized co-reactant along with the packaging of the material in an oxygen reduced environment may be addressed before sterilization.

Depending on the selected oxidizing agent or technique, a variety of degrees of oxidation, degrees of polymerization and oxidation sites may be utilized. For example, oxidation may be directed at a primary hydroxyl group (for example, the 6-hydroxyl group in the anhydroglucose units of glucans), resulting in carboxyl-polysaccharides with preserved ring structures. Oxidation may also be directed at a vicinal diol function present in a monosaccharide ring (for example, the C2-C3 site in anhydroglucose units), resulting in cleavage of the monosaccharide units and the production of dialdehyde functional groups. The dialdehyde content of such an oxidized polysaccharide may range from a degree of oxidation of, for example, 2% to virtually 100%, e.g., more than 30% or more than 50% of the available oxidation sites. The oxidized polysaccharide may also contain other functional groups, for example hydroxyalkyl groups, cationic groups, carboxyl groups and other acid groups. As a generalization, reduced amounts of oxidized polysaccharide may be employed as a co-reactant as the degree of polysaccharide oxidation is increased.

The polysaccharide, and the sterilized co-reactant, will normally be hydrated just prior to mixing the two parts together and placing the resulting fluid mixture in a treatment site. Hydration may be carried out by dissolving the polysaccharide in water or an aqueous solution containing any other desired ingredients. For example, normal saline solution and phosphate buffered saline solution (PBS) are preferred and readily available hydration solutions. The amount of polysaccharide in the hydrated solution may depend in part on the polysaccharide molecular weight, and may for example be about 1 to about 20%, about 1 to about 10% or about 1 to about 5% based on the solution weight. Additionally, the molar concentration of the sterilized polysaccharide in solution may for example be in the range of about 2% to 5%.

The polysaccharide and sterilized co-reactant may for example be combined in a molar ratio of about 20:1 to about 1:20, about 10:1 to about 1:10, about 5:1 to about 1:10, about 3:1 to about 1:5 or about 20:1. Once the first and second part have been mixed, a crosslinking reaction preferably is substantially complete within a few minutes (e.g., less than 5 minutes, less than 3 minutes, less than 2 minutes or less than 1 minute) after the start of mixing, yielding an initially fluid protective layer that desirably will not drip or run from a target area on a body temperature vertical skin surface.

The applied composition may fill the treatment site (e.g., a nasal or sinus cavity, or an opening, recess, passageway or joint in a portion of the limbs or spinal column), in which case the disclosed protective layer may be very thick with differing thicknesses throughout the layer and is not exposed to air or other nearby gases. The disclosed composition may also be applied as a thin film or other conformal coating in which case the disclosed protective layer may be relatively thin and exposed to air or other nearby gases, and with a substantially uniform thickness throughout the layer. The protective layer will desirably form a gel or a solid.

The protective layer desirably adheres to mucosal or other natural tissues (e.g., cartilage or bone) at the treatment site and resists detachment or other disruption until natural degradation or resorption of the layer takes place, e.g., after a residence time in vivo of from one to a few (e.g., 2, 3 or 4) days, weeks or months. Meanwhile bacterial recolonization or reinfection may be significantly reduced or prevented, and improved healing and reciliation may take place.

The protective layer may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, and the like. These advantages may arise due to a variety of mechanisms including a) killing bacteria, b) inhibiting bacterial colonization, c) inhibiting the adherence of bacteria to tissue, d) reducing tissue morbidity or abscess formation, e) reducing or preventing disease recurrence (for example, specifically reducing the chronic inflammation related to bacterial toxin and EPS), f) coating and protecting tissue during healing, such as by maintenance of a moist wound which promotes platelet aggregation, or by closure of a dry wound without excessive scabrous formation, g) hemostasis, h) optimizing the environment for reciliation of the mucosa, i) speeding the growth or regrowth of cilia and j) delivering therapeutic agent(s) to the treatment site. Desirably the protective layer will adhere to a portion of the mucosa while leaving the cilia in unadhered portions free to undergo natural rhythmic cilia motion (viz., cilia beating), will if desired also deliver antimicrobial agents or additional therapeutic agents, and desirably will discourage or prevent bacteria from adhering to the treatment site.

The disclosed composition may optionally include a variety of other ingredients before or after hydration. Exemplary other ingredients include nonaqueous solvents, acids, bases, buffering agents, antimicrobial agents, therapeutic agents and other adjuvants. An acid, base or buffering agent may for example maintain the composition, protective layer or both at an appropriate pH for contacting human tissue, e.g., a pH greater than 4.5, a near-neutral pH, or a pH less than 8.5. Exemplary buffering agents include barbitone sodium, glycinamide, glycine, potassium chloride, potassium phosphate, potassium hydrogen phthalate, sodium acetate, sodium citrate, sodium phosphate and their conjugate acids.

The disclosed compositions desirably are inherently antimicrobial without requiring addition of a separate antimicrobial agent. Antimicrobial activity in chitosan containing compositions may be influenced by the proportion of chitosan or chitosan derivatives in the composition (with higher proportions tending to provide greater antimicrobial activity) and by the number of available chitosan amine groups. In any event, a separate antimicrobial agent may be employed if desired.

Exemplary therapeutic agents which may be employed in the disclosed compositions include any material suitable for use at the intended treatment site including analgesics, anti-cholinergics, anti-fungal agents, antihistamines, steroidal or non-steroidal anti-inflammatory agents, anti-parasitic agents, antiviral agents, biostatic compositions, chemotherapeutic/antineoplastic agents, cytokines, decongestants, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art.

Other adjuvants that may be included in the disclosed compositions include dyes, pigments or other colorants; indicators; flavoring or sweetening agents including but not limited to anise oil, cherry, cinnamon oil, citrus oil, cocoa,

*eucalyptus*, herbal aromatics, lactose, maltose, menthol, peppermint oil, saccharine, sodium cyclamate, spearmint oil, sorbitol, sucrose, vanillin, wintergreen oil, xylitol and mixtures thereof; antioxidants; antifoam agents; and rheology modifiers including thickeners and thixotropes. The disclosed compositions desirably do not contain ingredients which might potentially harm mucosal tissues or structures, e.g., tissues in the nasal or sinus cavities.

The invention is further illustrated in the following non-limiting examples.

EXAMPLES

Test Procedures

Characterization of Impurities Test. $^1$H NMR spectroscopy was used to characterize the removal of impurities from a polysaccharide. The $^1$H NMR measurement was performed on a Varian MR-400 Spectrometer (Varian, Inc, Palo Alto, Calif.) at 70° C. using a classical $^1$H NMR approach with partial removal of an HOD peak. The sequences used to measure the spectra are listed in the following Table 1:

| Command | $^1$H NMR |
|---|---|
| NS | 16 |
| Rg | 128 |
| P1 | 3 us@-3 db |
| Sw | 5.5 ppm |
| O1p | 4.71 ppm |
| Td | 8k |
| D1 | 1 s |
| Temperature | 343 K |

An integration ratio ($I_{3.9}/I_{4.5}$) was determined from the resulting spectra using the region between δ 3.92 ppm to δ 3.94 ppm associated with certain impurities such as glycolic acid and the 4.5 ppm region associated with the assigned proton at the 1-C position.

Viscosity Measurement Test

The sample of a polysaccharide was prepared by placing a 1 ml solution of carboxymethyl chitosan in saline into 1.5-ml Eppendorf tubes. The tubes were inserted into a centrifuge and run at 13000 rpm for 10 min. The supernatant was recovered for viscosity measurement using an AR1000 Rheometer (TA Instruments, LTD, New Castle, Del.). The rheometer was used with a 40 mm SST plate and at a temperature of 25° C. The setting for the rheometer included: Normal force at 5.000 N, Normal force tolerance at 1.000 N, Gap change limit down at 100 um, Gap change limit up at 100 um, and Zero gap. About 1.4 mL of supernatant was used for the sample. The viscosity was recorded at a speed of 20/s.

Percent Solids Measurement

Percent solids of the polysaccharide was measured by thermogravimetric analysis to characterize the solubility of a polysaccharide. A supernatant of a polysaccharide was obtained in the manner used for the Viscosity Measurement Test. The TGA Q500 (TA Instruments, LTD, New Castle, Del.) was used to test 50 microliters of the supernatant. The material was placed into the machine. The ramp speed was set at 20° C. per minute up to a maximum temperature of 160° C. Isotherms were calculated every 5 minutes. A percent solids reading was then generated.

Gel Time Test

The gel time was determined by filling a 3-mL syringes 1 mL of carboxymethyl chitosan and another 3 mL syringe with 1 mL of starch solution. The syringes were then installed on a syringe holder and connected to a Micromedics SA-3652 Sprayer (Micromedics, Inc, St Paul, Minn.). The solutions were sprayed into a 4" weigh boat using 6 psi compressed air. The timer was started when all of the syringes were empty. The solution mixture was agitated horizontally and gel time was recorded until the gel stopped flowing.

Example 1 and Comparative Example 1

For example 1, carboxymethyl chitosan (CMC) was purchased from HMC$^+$ (Halle, Germany). A 20 gram sample of CMC was dissolved in 800 ml of deionized water under mechanical stirring. After the dissolution was complete, the solution was placed in a Spectra/Por dialysis membrane (1600 ml, MWCO:3500, Spectrum Laboratories, Inc., Rancho Dominguez, Calif.). The dialysis was performed in a 40-L container against deionized water for 20 hours. The water was changed 4 times during first 4 hours. The dialyzed solution was then lyophilized, vacuum dried at 55° C., and ground into powder using a coffee grinder. The moisture content of the CMC was about 3% by weight. A portion of the CMC was removed and subjected the Characterization of Impurities Test. The purified and sterilized CMC exhibited an integration ratio of 0.59. The remainder of the CMC was packed into a 3-mL syringe and placed in a foil pouch. The pouch was sealed after 3 times nitrogen purge. The oxygen level in the pouch was determined to be 0% using a 6600 Headspace Oxygen/Carbon Dioxide Analyzer (Illinois Instruments, Johnsburg, Ill.). The packaged CMC powder was sterilized at Beam One LLC (San Diego, Calif.) using E-Beam radiation at a target value of 25-kgy. The Example was repeated to create enough CMC packages for testing at intervals of 0, 2, 4, 6, and 24 months.

After each of the predetermined storage periods, the CMC of Example 1 then hydrated for testing. The sterilized CMC was joined with another syringe filled with 3 mL of saline using a syringe connector. The CMC and saline were mixed by transferring the materials back and forth between syringes. Air was periodically removed by disconnecting the syringe connector and forcing air out of the syringe with the plunger.

Comparative Example 1 was produced the same manner of example 1 with the exception that the solution was not subjected to filtration with a dialysis membrane prior to lyophilization. The moisture content of the CMC in Comparative Example 1 was about 10% by weight. Additionally, Comparative Example 1 was packed without a nitrogen purge. In the same manner as Example 1, Comparative Example 1 was repeated to create enough CMC packages for testing at intervals of 0, 2, 4, 6, and 24 months.

Example 1 and Comparative Example 1 were each subjected to the Gel Time Test, the Viscosity Measurement Test, and the Percent Solid Measurement. The results for each of the test are listed in Table 2. The purified and sterilized CMC of Example 1 showed substantially no change in Gel Time while Comparative Example 1 exhibits an increase in Gel Time by over a factor of 4. Example 1 also exhibited little change in viscosity over time while Comparative Example 1 showed wide variation. The change in solids content of Example 1 was less than 50%.

TABLE 2

| Conditions | | Comparative Example 1 | Example 1 |
|---|---|---|---|
| 0 month | Gel time (s) | 13 | 5 |
| | Viscosity (Pa · s) | 0.16 | 0.48 |
| | Percent solid (%) | 3.4 | 3.5 |
| 2 month | Gel time (s) | 33 | 7 |
| | Viscosity (Pa · s) | 0.048 | 0.46 |
| | Percent solid (%) | 3.4 | 3.5 |
| 4 month | Gel time (s) | 39 | 5 |
| | Viscosity (Pa · s) | 0.053 | 0.45 |
| | Percent solid (%) | 3.3 | 3.6 |
| 6 month | Gel time (s) | 47 | 6 |
| | Viscosity (Pa · s) | 0.048 | 0.46 |
| | Percent solid (%) | 3.1 | 3.6 |
| 24 month | Gel time (s) | 57 | 5 |
| | Viscosity (Pa · s) | 0.058 | 0.42 |
| | Percent solid (%) | 1.6 | 3.6 |

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

What is claimed is:

1. A method comprising: (a) providing a polysaccharide, (b) removing at least a portion of impurities from a manufacturing process of the polysaccharide to obtain an integration ratio of 1 or less, wherein the integration ratio is capable of being evaluated using $^1$H NMR spectroscopy by comparing a first value of a peak between about δ 3.92 ppm and about δ 3.94 ppm with a second value of a reference peak at about δ 4.5 ppm, (c) drying the polysaccharide to a moisture content of 7% by weight or less, (d) packaging the polysaccharide in less than 2% oxygen, and (e) sterilizing the polysaccharide with ionizing radiation to provide a sterilized polysaccharide, wherein the sterilized polysaccharide is soluble and has an extended shelf life having less than a 50% change in solids content after nine months as measured using the Percent Solids Measurement.

2. The method according to claim 1, wherein the method results in less than a 50% change in viscosity after nine months as measured using the Viscosity Measurement Test.

3. The method according to claim 2, wherein the method results in less than a 25% change in solids content of the polysaccharide after nine months as measured using the Percent Solids Measurement.

4. The method according to claim 1, wherein removing at least some impurities comprises at least one of filtration, membrane dialysis or precipitation.

5. The method according to claim 1, wherein the impurities include an organohalide compound, a glycolic acid or a salt or ester thereof, or an inorganic salt.

6. The method according to claim 1, wherein removing at least some impurities from the polysaccharide comprises removing chloroacetic acid, glycolic acid, or both, so as to obtain an integration ratio of about 0.7 or less, wherein the integration ratio is determined by the value of a peak at about 3.92 ppm through 3.94 ppm to a value of a reference peak of about 4.5 ppm as measured via $^1$H NMR.

7. The method according to claim 2, wherein the shelf life at room temperature is greater than 18 months.

8. The method according to claim 1, wherein drying includes lyophilization, convection drying, vacuum drying or a combination thereof.

9. The method according to claim 1, wherein the moisture content of the polysaccharide after drying is less than 3% by weight.

10. The method according to claim 1, wherein the polysaccharide is selected from the group consisting of alginate, carrageenan, cellulose, chitin, chitosan, carboxymethyl chitosan, chitosan succinimide, chondroitin sulfates, dextran, galactomannan, glycogen, hyaluronic acid, starch, heparin, or mixtures thereof.

11. The method according to claim 10, wherein the polysaccharide is carboxymethyl chitosan.

12. The method according to claim 1, wherein the polysaccharide is comminuted prior to packaging the polysaccharide.

13. The method according to claim 1, wherein packaging comprises placing the polysaccharide in a container and sealing the container in a polymeric enclosure.

14. The method according to claim 13, wherein the polysaccharide is chitosan.

15. The method according to claim 1, wherein a hydrogel is capable of being formed upon hydration of the sterilized polysaccharide and then reacting the hydrated polysaccharide with a sterilized co-reactant.

* * * * *